United States Patent
Drew

(10) Patent No.: US 11,660,393 B2
(45) Date of Patent: May 30, 2023

(54) EMERGENCY MANAGEMENT IMPLANTABLE DRUG DELIVERY SYSTEMS

(71) Applicant: Medtronic, Inc., Minneapolis, MN (US)

(72) Inventor: Touby A. Drew, Golden Valley, MN (US)

(73) Assignee: Medtronic, Inc., Minneapolis, MN (US)

( * ) Notice: Subject to any disclaimer, the term of this patent is extended or adjusted under 35 U.S.C. 154(b) by 485 days.

(21) Appl. No.: 16/857,850

(22) Filed: Apr. 24, 2020

(65) Prior Publication Data

US 2021/0330884 A1 Oct. 28, 2021

(51) Int. Cl.
*A61M 5/172* (2006.01)
*A61K 31/137* (2006.01)
*A61K 31/195* (2006.01)
*A61K 31/222* (2006.01)
*A61K 31/485* (2006.01)
(Continued)

(52) U.S. Cl.
CPC ......... *A61M 5/1723* (2013.01); *A61K 31/137* (2013.01); *A61K 31/195* (2013.01); *A61K 31/222* (2013.01); *A61K 31/485* (2013.01); *A61M 5/1407* (2013.01); *A61M 5/14276* (2013.01); *A61M 2205/18* (2013.01); *A61M 2205/3584* (2013.01); *A61M 2205/52* (2013.01); *A61M 2205/581* (2013.01); *A61M 2205/582* (2013.01); *A61M 2205/583* (2013.01); *A61M 2205/8206* (2013.01); *A61M 2230/00* (2013.01)

(58) Field of Classification Search
None
See application file for complete search history.

(56) References Cited

U.S. PATENT DOCUMENTS

| 4,987,897 | A | 1/1991 | Funke |
| 2002/0042446 | A1* | 4/2002 | Dewey ................. A61K 31/165 514/561 |

(Continued)

FOREIGN PATENT DOCUMENTS

| EP | 3586893 A1 | 6/2019 |
| WO | WO2004/058337 | 7/2004 |
| WO | WO-2004058337 A1 * | 7/2004 .......... A61M 25/007 |

OTHER PUBLICATIONS

PCT International Search Report and Written Opinion corresponding to PCT/US2021/028665 dated Aug. 9, 2021.

*Primary Examiner* — Manuel A Mendez
(74) *Attorney, Agent, or Firm* — Patterson Thuente, P.A.

(57) ABSTRACT

An implantable emergency management drug delivery system configured to deliver a medicament to reverse the effects of a drug overdose. The implantable emergency management drug delivery system including an implantable infusion pump configured to infuse a first medicament, and an emergency handling device having at least one physiological sensor configured to monitor a condition of a patient for a possibility of an overdose from the first medicament, a communication module configured to communicate the possibility of an overdose to the implantable infusion pump, and an implantable medicament delivery mechanism configured to deliver a second medicament to reduce one or more adverse physiological effects of the first medicament.

15 Claims, 5 Drawing Sheets

(51) Int. Cl.
*A61M 5/14* (2006.01)
*A61M 5/142* (2006.01)

(56) References Cited

U.S. PATENT DOCUMENTS

| | | | | |
|---|---|---|---|---|
| 2005/0070875 A1* | 3/2005 | Kulessa | ................ | B01F 25/433 |
| | | | | 604/500 |
| 2015/0352283 A1* | 12/2015 | Galasso | ............. | A61B 5/14532 |
| | | | | 604/65 |
| 2018/0147343 A1* | 5/2018 | Tyson | ............... | A61M 5/14276 |
| 2019/0374139 A1 | 12/2019 | Kiani et al. | | |

* cited by examiner the medicament delivery capabilities of the implantable medical pump or port to alleviate drug dosing risks to a patient. In some embodiments, the present disclosure enables the administration of an opioid overdose reversal drug (e.g., naloxone), should an overdose condition be detected in the patient. In other embodiments, the present disclosure enables the administration of one or more medicaments to mitigate the risk of a potential drug underdose.

EMERGENCY MANAGEMENT IMPLANTABLE DRUG DELIVERY SYSTEMS

TECHNICAL FIELD

The present technology is generally related to implantable medical devices, and more particularly to implantable drug delivery.

BACKGROUND

Implantable medical devices, such as implantable medical pumps and ports, are useful in managing the delivery and dispensation of prescribed therapeutic agents, nutrients, drugs, medicaments such as antibiotics, blood clotting agents, analgesics and other fluid or fluid like substances (collectively "medicaments" or "infusates") to patients in volume- and time-controlled doses as well as through boluses. Such implantable pumps and ports are particularly useful for treating conditions, diseases and disorders that require regular or chronic (i.e., long-term) pharmacological intervention, including managing chronic pain, tremor, spasticity, and pulmonary arterial hypertension, among others. Depending upon their specific designs and intended uses, implantable pumps and ports are well adapted to administer infusates to specific areas within the vasculature and central nervous system of a patient, as well as providing access to those spaces for aspiration.

Such implantable pumps and ports are typically implanted at a location within the body of a patient (typically a subcutaneous region in the lower abdomen) and are connected to a catheter configured for targeted drug delivery to specific areas within the patient, particularly those areas where the medicament is most effective, thereby minimizing the quantity of medicament necessary to achieve the desired therapeutic effect. Further, as many implantable pumps infuse the medicament according to programmed parameters, implantable pumps avoid the problem of patient noncompliance, namely the patient failing to take the prescribed drug or therapy as instructed.

Although implantable pumps and ports have proven quite effective, introducing certain classes of drugs into the human body can present serious risks to the health and safety of the patient, particularly where external factors may be influencing the patient's ability to adequately absorb and process the quantity of the infused drug. For example, where the implantable pump or port is configured to infuse opioids for the management of chronic pain, an upper infusion limit is established to an prevent accidental overdose. However, if the patient ingests an additional supply of opioids (e.g., beyond what has been prescribed), infusion of the prescribed dose of opioid by the implantable pump or port may result in harm to the patient. Similar risks may be present with the infusion of other types of drugs, such as baclofen for the treatment of tremor and spasticity and Remodulin™ (treprostinil) for the treatment of pulmonary arterial hypertension, the use of which additionally presents an underdose risk.

Applicants of the present disclosure have developed systems and methods to address these concerns.

SUMMARY OF THE DISCLOSURE

The techniques of this disclosure generally relate to implantable emergency management drug delivery systems and methods including an emergency handling device configured to communicate with an implantable medical pump or port to selectively augment the medicament delivery capabilities of the implantable medical pump or port to alleviate drug dosing risks to a patient. In some embodiments, the present disclosure enables the administration of an opioid overdose reversal drug (e.g., naloxone), should an overdose condition be detected in the patient. In other embodiments, the present disclosure enables the administration of one or more medicaments to mitigate the risk of a potential drug underdose.

Accordingly, in some embodiments, the emergency handling device can serve as a backup system to one or more implantable medical pumps or ports, thereby enabling the administration of a potentially life-saving quantity of drug, where external factors may be influencing the patient's ability to process a quantity of delivered medicament or where an occlusion or other malfunction occurs in the implantable medical pump or port inhibiting delivery of medicament according to the prescribed therapeutic treatment. In other embodiments, the emergency handling device can be configured to operate independently from an implantable medical pump or port, primarily as a safeguard against overdose or underdose risks (e.g., to counteract potentially harmful effects from opioids taken by the patient). In all embodiments, the emergency handling device can be configured to operate without human intervention, thereby enabling an emergency delivery medicament, even when the patient is alone and unconscious.

In embodiments, the emergency handling device can include a refillable, pressurized single-dose medicament reservoir with minimal electronics, thereby enabling the device to be small in size, particularly in comparison to a conventional implantable medical pump. For example, in one embodiment, the emergency handling device can have a volume of less than about 5 cc. In some embodiments, the emergency handling device can be configured to communicate with one or more external sensors (e.g., smart watch, wrist band tracker, sensors embedded in clothing, etc.) as an aid in monitoring one or more physiological conditions of the patient. Further, in some embodiments, the emergency handling device can be configured to provide alerts, notifications and messages to the patient and healthcare providers based on monitored conditions, events and other factors.

One embodiment of the present disclosure provides an implantable emergency management drug delivery system configured to deliver a secondary medicament to reverse the effects of overdose from a primary medicament. The implantable emergency management drug delivery system can include an implantable infusion pump configured to infuse a first medicament and an emergency handling device. The emergency handling device can include at least one physiological sensor configured to monitor a condition of a patient for a possibility of an overdose from the first medicament, a communication module configured to communicate the possibility of an overdose to the implantable infusion pump, and an implantable medicament delivery mechanism configured to deliver a second medicament to reduce one or more adverse physiological effects of the first medicament.

In one embodiment, the first medicament is an opioid and the second medicament is a medicament capable of reversing the effects of opioids. In one embodiment, the implantable medicament delivery mechanism includes a pressurized medicament reservoir and a medicament delivery valve, wherein opening of the medicament delivery valve causes medicament within the pressurized medicament reservoir to be expelled into tissue surrounding the implantable medicament delivery mechanism. In one embodiment, the implantable medicament delivery mechanism contains a refillable medicament reservoir. In one embodiment, the at least one physiological sensor is an externally wearable device.

Another embodiment of the present disclosure provides an implantable emergency management drug delivery system configured to communicate with an implantable infusion pump to inhibit the likelihood of an overdose. The implantable emergency management drug delivery system can include an implantable infusion pump configured to administer medicament at an infusion rate, and an emergency handling device. The emergency handling device can include at least one physiological sensor configured to monitor a condition of a patient for a possibility of a medicament overdose, and a communication module configured to communicate with the implantable infusion pump to at least one of temporarily pause or slow the medicament infusion rate to address the possibility of the medicament overdose.

In one embodiment, the medicament is at least one of an opioid or treprostinil. In one embodiment, the at least one physiological sensor is an externally wearable device.

Another embodiment of the present disclosure provides an implantable emergency management drug delivery system configured to deliver a medicament to inhibit an unintentional underdose of medicament. The implantable emergency management drug delivery system can include an implantable infusion pump configured to infuse a medicament, and an emergency handling device. The emergency handling device can include at least one physiological sensor configured to monitor a condition of a patient for a possibility of a medicament underdose, and a medicament delivery mechanism configured to deliver an additional supply of medicament to address the possibility of the medicament underdose.

In one embodiment, the medicament is at least one of baclofen or treprostinil. In one embodiment, both the implantable infusion pump and emergency handling device are configured to deliver medicament through a shared catheter. In one embodiment, the at least one physiological sensor is an externally wearable device.

Another embodiment of the present disclosure provides an implantable emergency management drug delivery system configured to inhibit an unintentional underdose of medicament. The implantable emergency management drug delivery system can include a first implantable infusion pump configured to infuse medicament and a second implantable infusion pump configured to infuse medicament. The first implantable infusion pump can include a communication module configured to receive infusion information from the second implantable infusion pump, and the second implantable infusion pump can include a communication module configured to receive infusion information from the first implantable infusion pump. Each of the first and second implantable pumps can further include a processor configured to determine if a total medicament infusion rate by both the first and second implantable infusion pumps falls below an underdose threshold. Additionally each of the first and second implantable pumps can include a delivery mechanism configured to increase the medicament infusion rate to ensure delivery of a total volume of medicament at or above the underdose threshold.

In one embodiment, the medicament is intrathecally delivered baclofen. In one embodiment, the delivery mechanism includes a medicament pump and refillable reservoir.

Another embodiment of the present disclosure provides an implantable emergency management drug delivery system configured to deliver a potentially life-saving dose of medicament and alert others to a physical location of a patient, upon determining that the patient is suffering from at least one of a drug overdose or an allergic reaction. The implantable emergency management drug delivery system can include an emergency handling device having at least one physiological sensor configured to monitor a condition of a patient for at least one of a possibility of a drug overdose or an allergic reaction, an implantable medicament delivery mechanism configured to deliver medicament as a treatment for at least one of a drug overdose or allergic reaction, a location module configured to determine a physical location of the patient, and a communication module configured to send an alert to an external device identifying a physical location of the patient.

In one embodiment, the medicament is at least one of naloxone, a steroid, an allergy medicament such as an antihistamine, or alpha-agonist such as synthetic epinephrine. In one embodiment, the implantable medicament delivery mechanism includes a pressurized medicament reservoir and a medicament delivery valve, wherein opening of the medicament delivery valve causes medicament within the pressurized medicament reservoir to be expelled into tissue surrounding the implantable medicament delivery mechanism. In one embodiment, the implantable medicament delivery mechanism includes a refillable medicament reservoir. In one embodiment, the at least one physiological sensor is an externally wearable device.

The details of one or more aspects of the disclosure are set forth in the accompanying drawings and the description below. Other features, objects, and advantages of the techniques described in this disclosure will be apparent from the description in the drawings, and from the claims.

BRIEF DESCRIPTION OF THE DRAWINGS

The disclosure can be more completely understood in consideration of the following detailed description of various embodiments of the disclosure, in connection with the accompanying drawings, in which.

Figure 1:
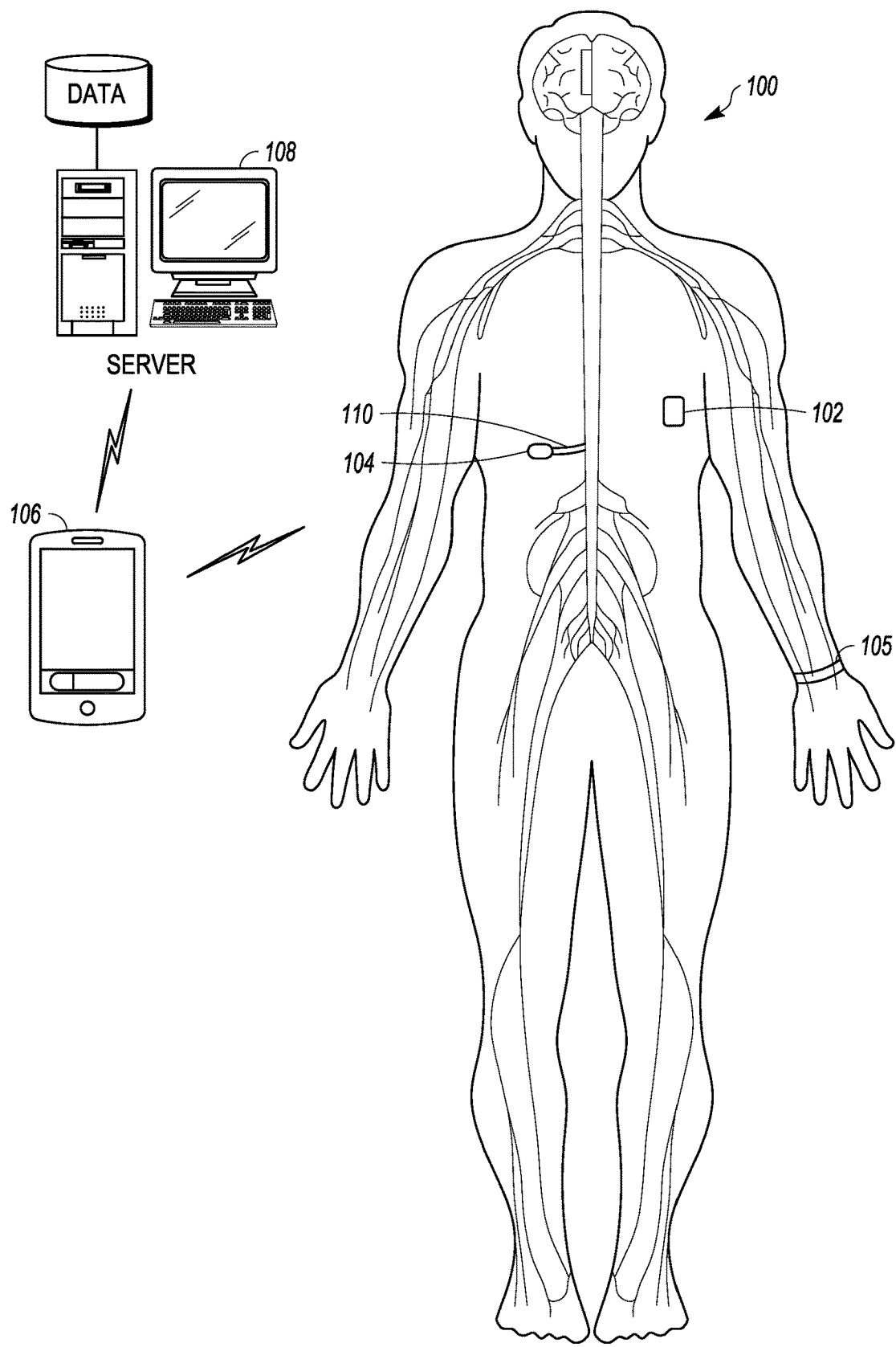
FIG. 1 is a schematic view depicting an implantable emergency management drug delivery system, in accordance with an embodiment of the disclosure.

While embodiments of the disclosure are amenable to various modifications and alternative forms, specifics thereof shown by way of example in the drawings will be described in detail. It should be understood, however, that the intention is not to limit the disclosure to the particular embodiments described. On the contrary, the intention is to cover all modifications, equivalents, and alternatives falling within the spirit and scope of the subject matter as defined by the claims.

DETAILED DESCRIPTION

Referring to FIG. 1, an implantable emergency management drug delivery system 100, including an emergency handling device 102 configured to communicate with an implantable infusion pump 104 to alleviate drug dosing risks, is depicted in accordance with an embodiment of the disclosure. In some embodiments, the implantable emergency management system 100 can further include an optional external programmer 106 and optional server 108 configured to communicate with at least one of the emergency handling device 102 or implantable infusion pump 104. Further, in some embodiments, the implantable emergency management system 100 can include one or more external physiological sensors 105, which can be in communication with the emergency handling device 102, implantable infusion pump 104, optional external programmer 106, and optional server 108.

Figure 2A:
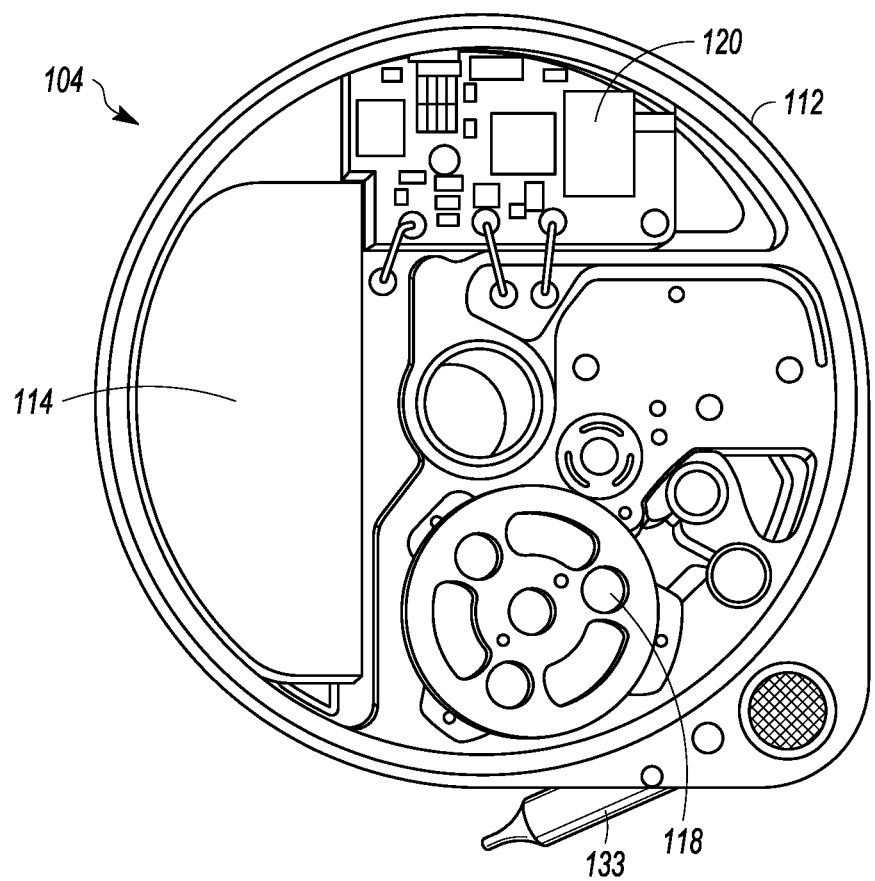
FIG. 2A is a cross-sectional schematic plan view depicting an implantable medicament pump, in accordance with an embodiment of the disclosure.
Figure 2B:
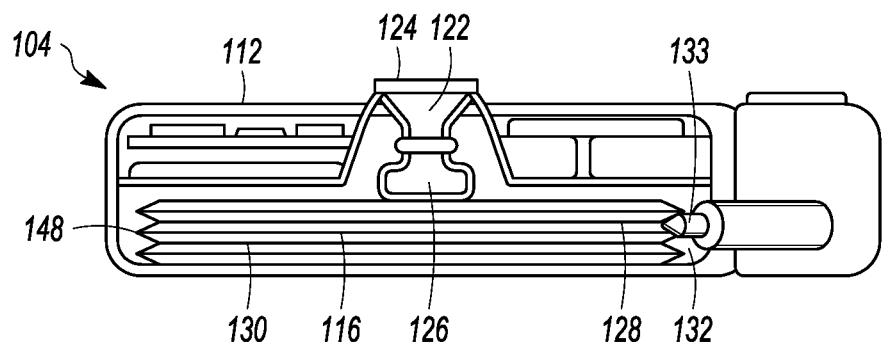
FIG. 2B is a cross-sectional schematic profile view depicting the implantable medicament pump of FIG. 2A.

As depicted, the implantable medical pump 104 can be implanted within the body of a patient, and can be in fluid communication with a catheter 110 having a distal tip positioned within the patient (e.g., within an intrathecal space, intracranial space, pulmonary artery, etc.) for targeted delivery of medicament. Referring to FIGS. 2A-B, cross sectional views of an implantable medical pump 104 configured to communicate with an emergency handling device 102 to alleviate drug dosing risks are depicted in accordance with an embodiment of the disclosure. The implantable medical pump 104 can generally include a housing 112, power source 114, medicament reservoir 116, medicament pump 118, and computing device 120. The housing 112 can be constructed of a material that is biocompatible and hermetically sealed, such as titanium, tantalum, stainless steel, plastic, ceramic, or the like.

The medicament reservoir 116 can be carried by the housing 112 and can be configured to contain medicament. In one embodiment, medicament within the medicament reservoir 116 can be accessed via an access port 122. Accordingly, the access port 122 can be utilized to refill, aspirate, or exchange fluid within the medicament reservoir 116. In some embodiments, the access port 122 can include a septum 124 configured to seal a port chamber 126 relative to an exterior of the housing 112. The septum 124 can be constructed of a silicone rubber or other material having desirable self-sealing and longevity characteristics. The port chamber 126 can be in fluid communication with the medicament reservoir 116.

The medicament reservoir 116 can include a flexible diaphragm 128. The flexible diaphragm 128, alternatively referred to as a bellows, can be substantially cylindrical in shape and can include one or more convolutions configured to enable the flexible diaphragm 128 to expand and contract between an extended or full position and an empty position. In one embodiment, the flexible diaphragm 128 can divide the medicament reservoir 116 into a medicament chamber 130 containing liquid medicament (within the flexible diaphragm 128), and a vapor chamber 132 (surrounding the flexible diaphragm 128).

As the medicament chamber 130 is filled with medicament, the flexible diaphragm 128 extends downwardly (with reference to FIG. 2B) toward a bottom portion of the housing 112 until it has reached a maximum volume or some other desired degree of fullness. Alternatively, as the medicament chamber 130 is aspirated, the flexible diaphragm 128 contracts upwardly toward a top portion of the housing 112 until the medicament chamber reaches a minimum volume. In one embodiment, the flexible diaphragm 128 can have a compression spring rate which tends to naturally bias the flexible diaphragm 128 towards an expanded position.

The medicament pump 118 can be carried by the housing 112. The medicament pump 118 can be in fluid communication with the medicament reservoir 116 and can be in electrical communication with the computing device 120. The medicament pump 118 can be any pump sufficient for infusing medicament to the patient, such as a peristaltic pump, piston pump, a pump powered by a stepper motor or rotary motor, a pump powered by an AC motor, a pump powered by a DC motor, electrostatic diaphragm, piezioelectric motor, solenoid, shape memory alloy, or the like.

The catheter 110 (as depicted in FIG. 1) can be operably coupled to the implantable medical pump 104 via catheter port 133, such that the lumen of the catheter 110 is in fluid communication with the medical pump 118 and reservoir 116. A distal tip of the catheter 110 can be positioned, for example, in a subarachnoid space, intracranial space, pulmonary artery, or other area within a patient, for targeted delivery of medicament.

Figure 3:
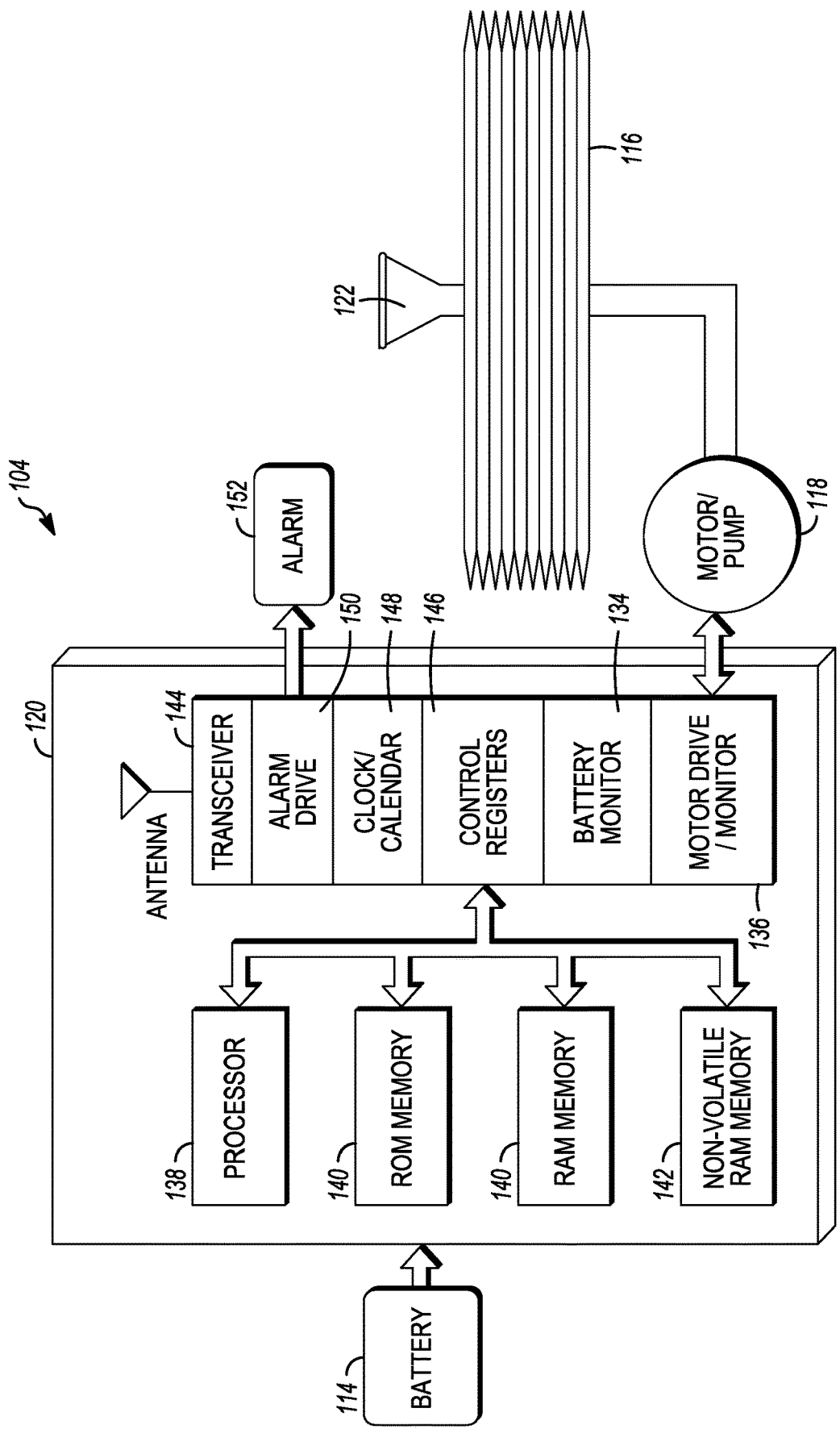
FIG. 3 is a schematic electrical diagram depicting an implantable medical pump, in accordance with an embodiment of the disclosure.

Referring to FIG. 3, a block diagram of an implantable medical pump 104 configured to communicate with an emergency handling device 102 to alleviate drug dosing risks is depicted in accordance with an embodiment of the disclosure. The computing device 120 can be carried in the housing 112 (as depicted in FIG. 2A) and can be in electrical communication with the medicament pump 118, and power source 114. The power source 114 can be a battery, such as a rechargeable lithium-ion battery. The power source 114, which can be monitored via the battery monitor 134, can be carried in the housing 112, and can selectively operate the medicament pump 118, and computing device 120. Control of the medicament pump 118 can be directed by a motor drive/monitor element 136.

The computing device 120 can include a processor 138, memory 140/142, and transceiver circuitry 144. In one embodiment, the processor 138 can be a microprocessor, logic circuit, Application-Specific Integrated Circuit (ASIC) state machine, gate array, controller, or the like. The computing device 120 can generally be configured to control infusion of medicament according to programmed parameters or a specified treatment protocol. The programmed parameters or specified treatment protocol can be stored in the memory 140/142 for specific implementation by a control register 146. A clock/calendar element 148 can maintain system timing for the computing device 120. In one embodiment, an alarm drive 150 can be configured to activate one or more notification, alert or alarm features, such as an illuminated, auditory or vibratory alarm 152.

The transceiver circuitry 144 can be configured to receive information from and transmit information to the emergency handling device 102, one or more wearable physiological sensors 105, external programmer 106, and server 108. The implantable medical pump 104 can be configured to receive programmed parameters and other updates from the external programmer 106, which can communicate with the implantable medical pump 104 through well-known techniques such as wireless telemetry, Bluetooth, or one or more proprietary communication schemes (e.g., Tel-M, Tel-C, etc.). In some embodiments, the external programmer 106 can be configured for exclusive communication with one or more implantable medical pumps 104. In other embodiments, the external programmer 106 can be any computing platform, such as a mobile phone, tablet or personal computer. In some embodiments, the implantable medical pump 104 and external programmer 106 can further be in communication with a cloud-based server 108. The server 108 can be configured to receive, store and transmit information, such as program parameters, treatment protocols, drug libraries, and patient information, as well as to receive and store data recorded by the implantable medical pump 104.

Figure 4A:
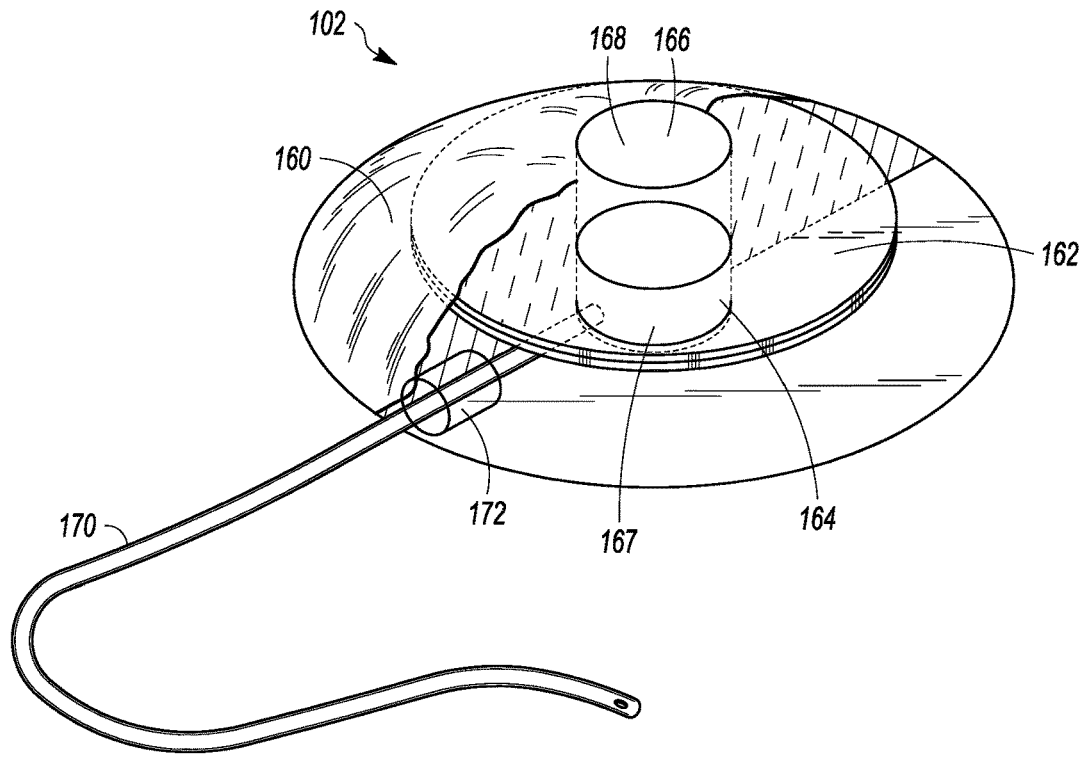
FIG. 4A is a partial cross-sectional schematic view depicting an emergency handling device, in accordance with an embodiment of the disclosure.
Figure 5:
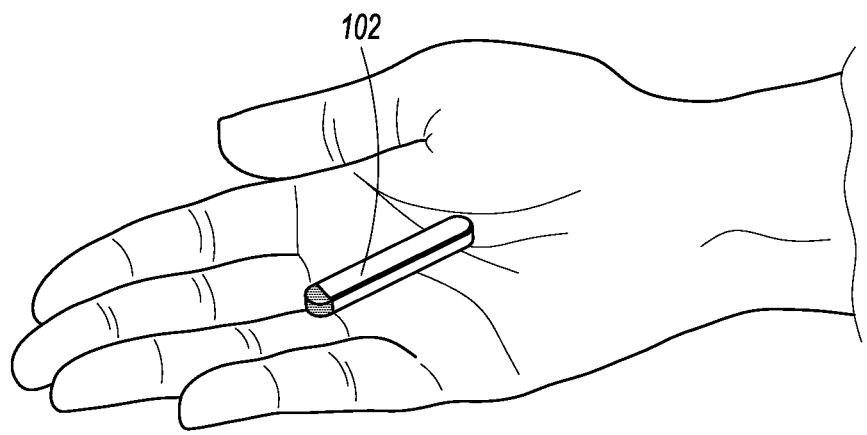
FIG. 5 is a perspective view depicting an emergency handling device configured to sense one or more physiological conditions of the patient, in accordance with an embodiment of the disclosure.

Referring to FIG. 4A, an emergency handling device 102 configured to communicate with an implantable infusion pump 104 to alleviate drug dosing risks, is depicted in accordance with an embodiment of the disclosure. In one embodiment, the emergency handling device 102 can include a housing 160, electrical circuitry 162, and medicament reservoir 164. In other embodiments, the emergency handling device 102 can be configured purely as a monitoring device (e.g., without a medicament reservoir) (such as that depicted in FIG. 5). In yet other embodiments, the emergency handling device 102 can include all the features of an implantable infusion pump (such as that depicted in FIGS. 2A-3). For example, in cases where a patient has a first infusion pump and a second infusion pump implanted within their body, the first infusion pump can serve as an emergency handling device for the second infusion pump, and the second infusion pump can serve as an emergency handling device for the first infusion pump.

With continued reference to FIG. 4A, the housing 160 can be constructed of a material that is biocompatible and hermetically sealed, such as titanium, tantalum, stainless steel, plastic, ceramic, or the like. In some embodiments, the emergency handling device 102 can be much smaller than the implantable infusion pump 104. For example, where an implantable infusion pump 104 may have a displacement volume of between about 50 cc to about 200 cc, emergency handling devices 102 of the present disclosure can have a displacement volume of less than about 5 cc, and in some cases can have a displacement of less than about 2.5 cc (particularly where the emergency handling device 102 does not include a medicament reservoir 164 such as that depicted in FIG. 5). In some embodiments, the emergency handling device 102 can be positioned beneath the skin of the patient or in tissue in a location remote from the implant pocket in which the implantable infusion pump 104 is positioned.

In embodiments including a medicament reservoir 164, the reservoir 164 can be carried by the housing 160 and can be configured to contain medicament. For example, in some embodiments, the reservoir 164 can be configured to contain a single dose of medicament to alleviate a drug dosing risk (e.g., potential overdose or drug underdose) or to address an physiological condition (e.g., low or labored respiration, abnormal heart rate, allergic reaction, etc.) experienced by a patient. A medicament reservoir 164 containing multiple doses of medicament is also contemplated. Additionally, the use of multiple single dose medicament reservoirs 164 is contemplated.

In one embodiment, medicament within the medicament reservoir 164 can be accessed via an access port 166, including a self-sealing septum 168 positioned beneath the skin of the patient. Accordingly, the access port 166 can be utilized to refill fluid within the medicament reservoir 164, thereby enabling the emergency handling device 102 to be recharged with medicament after use. Additionally, the access port 166 can be utilized to aspirate or exchange fluid within the medicament reservoir 164, thereby enabling the aspiration (e.g., prior to an MRI procedure) or replacement of medicament (e.g., medicament with an expiration date) without a need to explant the emergency handling device 102 from the patient.

In some embodiments, the medicament reservoir 164 can include a flexible diaphragm 167, configured to enable the medicament reservoir 164 to be expanded between an extended or full position and an empty position. In some embodiments, the flexible diaphragm 167 can include a spring or other mechanism configured to naturally bias the medicament reservoir 164 to the empty position. In such embodiments, the flexible diaphragm 167 can be expanded to the extended position by the introduction of pressurized medicament into the medicament reservoir. In embodiments with a pressurized reservoir 164, the emergency handling device 102 can include a medicament delivery valve 172, configured such that opening of the valve 172 causes medicament within the pressurized reservoir 164 to be expelled under a natural bias of the flexible diaphragm 166. Accordingly, embodiments of the present disclosure provide a simple drug delivery mechanism without the need for a medicament pump, flow regulation, monitoring of drug delivery, or the like.

Figure 6:
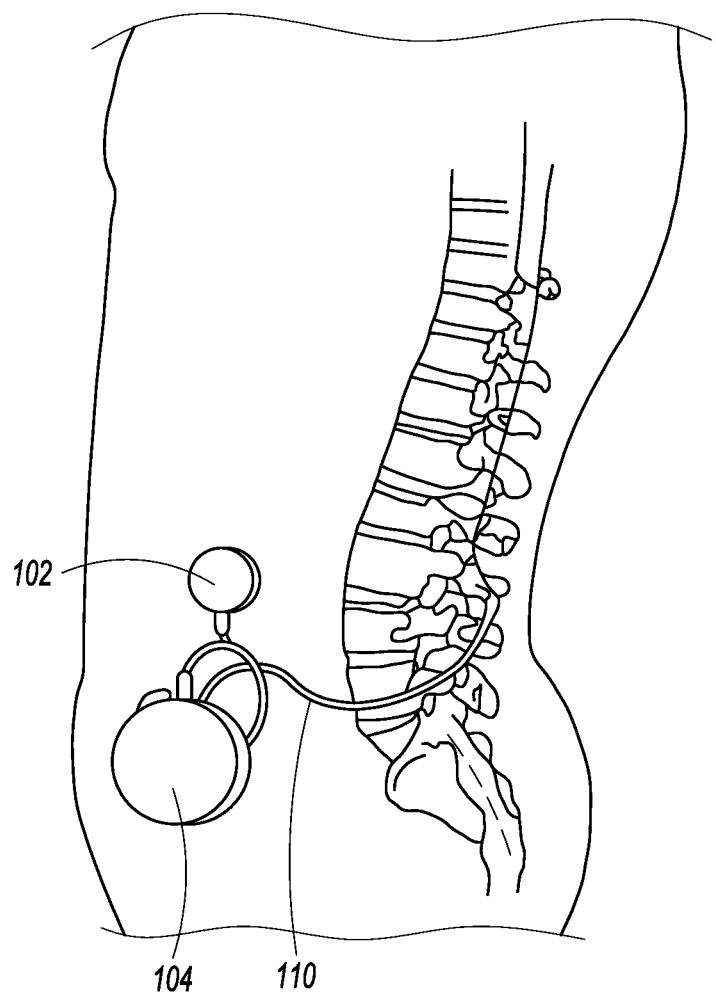
FIG. 6 is a perspective, schematic view an implantable emergency management drug delivery system configured to deliver one or more forms of medicament into an intrathecal space of a patient, in accordance with an embodiment of the disclosure.

In some embodiments the emergency handling device 102 can be configured to deliver medicament directly into tissue of the patient surrounding the emergency handling device 102, without the need for a catheter. In other embodiments, the emergency handling device 102 can be the operably coupled to a catheter 170 for targeted delivery of medicament into a specific area of the patient. For example, with reference to FIG. 6, in one embodiment, the emergency handling device 102 and implantable infusion pump 104 can be coupled to a single catheter 110. In some embodiments, the catheter 110 can be a single lumen catheter. In other embodiments, the catheter 110 can be a dual lumen catheter, with a first lumen dedicated to delivery of medicament from the implantable infusion pump 104 and a second lumen dedicated to delivery of medicament from the emergency handling device 102, thereby avoiding a need to surgically implant multiple catheters into areas desirable for targeted delivery of medicament (e.g., the intrathecal space, intracranial space, pulmonary artery, etc.).

Figure 4B:
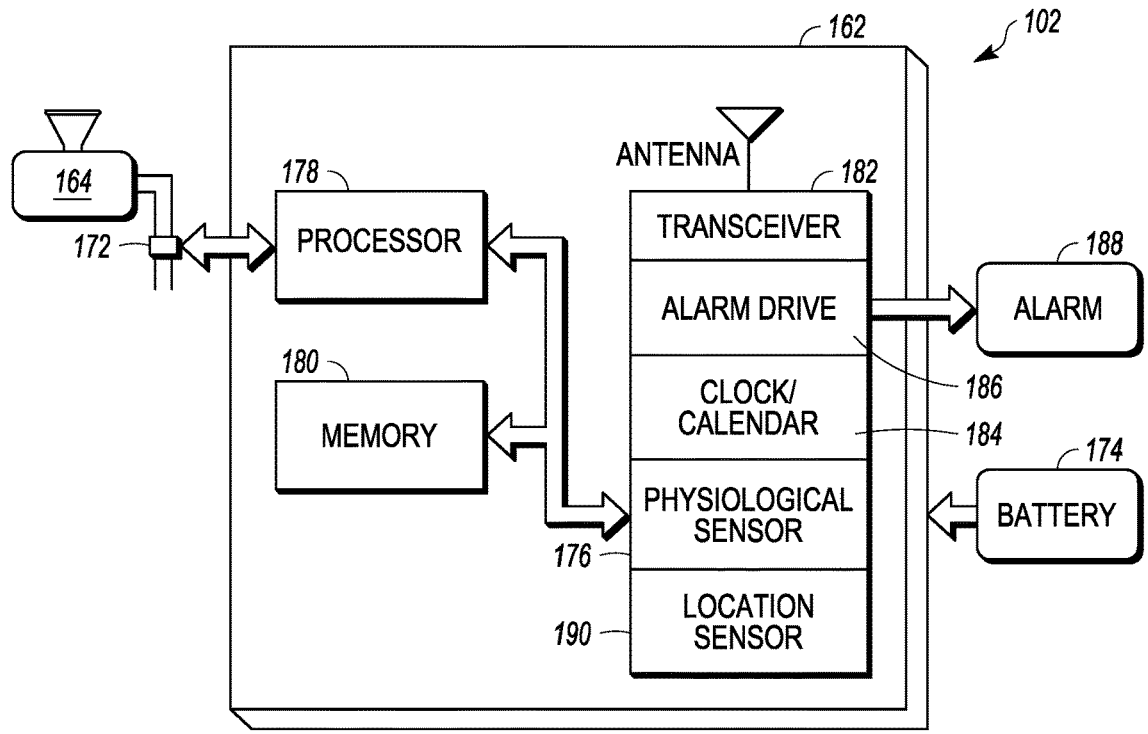
FIG. 4B is a schematic electrical diagram depicting an emergency handling device, in accordance with an embodiment of the disclosure.

Referring to FIG. 4B, a block diagram of an emergency handling device 102 configured to communicate with an implantable infusion pump 104 to alleviate drug dosing risks is depicted in accordance with an embodiment of the disclosure. The electrical circuitry 162 can be carried in the housing 160 and can be powered by a power source 174. The power source 174 can be a battery, such as a rechargeable lithium-ion battery. The electrical circuitry 162 can include one or more physiological sensors 176, processor 178, memory 180, and transceiver circuitry 182. In embodiments including a reservoir, a medicament delivery valve 172 can be connected to or in communication with the electrical circuitry 162.

The one or more physiological sensors 176 can include a heart rate sensor, respiration sensor, pulse oximeter, blood pressure sensor, intracranial pressure sensor, cerebral spinal fluid pressure sensor, intra-abdominal pressure sensor, temperature sensor, or the like. The processor 78 can be a microprocessor, logic circuit, Application-Specific Integrated Circuit (ASIC) state machine, gate array, controller, or the like. The transceiver circuitry 182 can be configured to receive information from and transmit information to the implantable medical pump 104, one or more external physiological sensors 105, external programmer 106, and server 108 through well-known techniques such as wireless telemetry, Bluetooth, or one or more proprietary communication schemes (e.g., Tel-M, Tel-C, etc.). In some embodiments, the electrical circuitry 162 can further include clock/calendar element 184 configured to maintain system timing, and an alarm drive 186 configured to activate one or more notification, alert or alarm features, such as an illuminated, auditory or vibratory alarm 188. In some embodiments, the electrical circuitry 162 can additionally include one or more geographical positional data sensors 190, thereby providing an indication of a location of a patient.

Accordingly, in some embodiments, the electrical circuitry 162 is configured to sense one or more physiological conditions of a patient, which can optionally trigger a response, such as activate one or more notification, alert or alarm features, communicating the sensed one or more physiological conditions to an external device, or manipulating the medicament delivery valve 172 for the administration of medicament. In some embodiments, the electrical circuitry 162 is further configured to receive input from one or more external physiological sensors 105, which can be worn by a patient (e.g., smart watch, wrist band tracker or other wearable technology, sensors embedded in clothing, etc.), carried by the patient (e.g., a smart phone, mobile computing device, etc.) or positioned in proximity to the patient (e.g., a stationary monitor, etc.), or affixed to the patient such as a patch sensor.

In some embodiments, the sensed one or more physiological conditions of a patient are compared to one or more defined thresholds or ranges of acceptable limits, such that a sensed physiological condition exceeding the defined threshold or falling outside of the range of acceptable limits triggers one or more response (e.g., sounding an alarm, transmitting data, administering medicament, etc.). In other embodiments, the sensed one or more physiological conditions can be transmitted to an external device without additional processing (e.g., without comparison to a defined threshold or range of acceptable limits). In other embodiments, one or more responses can be triggered according to a scheduled calendar event as determined by the clock/calendar element 184. In some embodiments, events (e.g., manipulation of the medicament delivery valve 172, sounding of the alarm 188) or data gathered by the one or more physiological sensors 176 can be logged in the memory 180 for future use.

In one embodiment, the emergency handling device 102 can be configured to address an opioid overdose, potential opioid overdose, or the likelihood that a opioid overdose may be occurring (collectively referred to herein as an "overdose event"). For example, in one embodiment, the one or more physiological sensor 176 of the emergency handling device 102 can be a respiratory monitor, pulse oximeter, or the like. Accordingly, if during operation the one or more physiological sensor 176 detects respiratory distress indicative of an overdose event, the emergency handling device 102 can communicate respiratory distress to the implantable infusion pump 104. If the implantable infusion pump 104 is presently delivering medicament in the form of an opioid, the implantable infusion pump 104 can temporarily pause, slow down or stop infusion. Alternatively, if the implantable infusion pump has already delivered a bolus of opioid, and it is no longer possible to pause, slow down or stop the infusion, the emergency handling device can deliver a dose of naloxone. Additionally, the emergency handling device 102 or implantable infusion pump 104 can issue a notification, alert, or alarm indicating the sensed respiratory distress, thereby alerting both the patient and caregiver to the sensed respiratory distress and the possibility of an opioid overdose.

In another embodiment, the emergency handling device 102 can be configured to deliver epinephrine in the event of an allergic reaction. For example, in one embodiment, the one or more physiological sensors of the emergency handling device 102 can be configured to monitor the patient's heart rate and respiratory rates. If during use, it is determined that the patient is likely suffering from an allergic reaction, the emergency handling device 102 can affect an administration of epinephrine, for example by opening the medicament delivery valve 172 and allowing medicament within the medicament reservoir 164 to be expelled into tissue of the patient surrounding the emergency handling device 102. Accordingly, in some embodiments, the emergency handling device 102 can be used as a standalone device, independent of an implantable infusion pump 104. Further, the emergency handling device 102 can be configured to deliver medicament without human intervention, thereby enabling the delivery of a potentially life-saving drug when a patient is alone and unconscious. In one embodiment, the emergency handling device 102 can further be configured to issue a notification, alert, or alarm indicating the possibility of an allergic reaction along with a location of the patient as determined by the location sensor 190.

In another embodiment, the emergency handling device can be configured to aid in regulating a dosage of baclofen to a patient. Overdose of baclofen, which is typically delivered intrathecally, is generally not a concern. However, under delivery of an expected dose of baclofen can be life-threatening. Accordingly, in some embodiments, the emergency handling device 102 can be configured to monitor the patient for signs of distress as a result of an underdose of baclofen. If it is determined that the patient is suffering from an underdose baclofen, the emergency handling device 102 can be configured to infuse a quantity of baclofen, potentially over an extended period of time (e.g., slow release).

In some cases, a patient may have more than one infusion pump configured to administer baclofen implanted, particularly where the baclofen is administered into different areas within the intrathecal space to address spasticity specific to those areas. In such cases, a first implantable infusion pump can serve as the emergency handling device for a second implantable infusion pump, and a second implantable infusion pump can serve as the emergency handling device for the first implantable infusion pump. Accordingly, each of the implantable pumps can monitor the other pump's performance to determine proper operation. If one pump determines that the other pump is experiencing a problem, the pump acting as the emergency handling device can direct the pump experiencing the problem to run diagnostics or reset in order to address the problem. Where the problem is unable to be fixed, and an underdose of baclofen is likely to occur, the pump acting as the emergency handling device can increase the quantity of baclofen delivered to the patient, thereby ensuring that the patient receives at least a minimum required dose of the medicament.

In another embodiment, the emergency handling device 102 can be configured to monitor one or more implantable infusion pumps 104 for information related to elective replacement or end of service (e.g., exhaustion of battery, depletion of medicament, abnormal decreases in rates of infusion, etc.). In such embodiments, the emergency handling device can be configured to alert both the user and caregivers to a potential problem with the one or more monitored implantable infusion pump 104.

In yet another embodiment, the emergency handling device 102 can be configured to aid in regulating a dosage of Remodulin™ (treprostinil) to a patient. Treprostinil has been found to be effective in resolving symptoms associated with pulmonary arterial hypertension. Remodulin is typically infused within a relatively narrow therapeutic envelope. Administration of treprostinil outside of the acceptable narrow therapeutic envelope can result in a potentially harmful drug overdose or drug underdose. Further, treprostinil is commonly infused into the vasculature of a patient (e.g., pulmonary artery); administration of treprostinil into muscle or other tissues typically results in a painful, inflammatory response.

Accordingly, in embodiments configured to regulate dosages of treprostinil, the emergency handling device 102 can be configured to monitor one or more physiological conditions of the patient for an underdose event or an overdose event. If it is determined that an overdose event is occurring, the emergency handling device 102 can instruct the implantable infusion pump 104 to temporarily pause or slow the rate of infusion of treprostinil. Alternatively, if it is determined that an underdose event is occurring, the emergency handling device 102 can be configured to infuse a quantity of treprostinil, potentially over an extended period of time (e.g., slow release). In some embodiments, emergency handling devices configured to administer treprostinil can be operably coupled to a central or periphery intravenous catheter, thereby enabling infusion of treprostinil into the vasculature of the patient.

In yet another embodiment, the emergency handling device 102 can be configured to aid in the administration of a class of drugs referred to as antisense oligonucleotides (ASOs) according to an intermittent schedule. ASOs have been researched as treatment options for genetic disorders, diseases and infections such as cancers (including lung cancer, colorectal carcinoma, pancreatic carcinoma, malignant glioma and malignant melanoma), diabetes, amyotrophic lateral sclerosis (ALS), Parkinson's disease, Duchenne muscular dystrophy, spinal muscular atrophy, Ataxia-telangiectasia, as well as diseases such as asthma, arthritis and pouchitis. ASOs are typically intermittently delivered according to a defined schedule (e.g., once a week for four weeks, followed by once a month for four months). In some embodiments, the clock/calendar element 184 of the emergency handling device 102 can regulate release of stored doses of ASO according to the defined intermittent schedule, thereby enabling the patient greater flexibility while receiving ASO therapy. Accordingly, in some embodiments, the emergency handling device 102 can be configured for precise delivery of intermittent therapy in the absence of a caregiver.

The specific examples described above represent just a few of a wide variety of example embodiments and should not be considered limiting. Use of the emergency handling device 102 to report and monitor other patient conditions or events, and to administer other types of medicaments is also contemplated.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A system comprising:
   a first device comprising a first delivery mechanism configured to infuse a medicament into a patient;
   a second device comprising a second delivery mechanism configured to infuse a second the medicament into the patient, wherein:
      the first device comprises a first communication module configured to receive first infusion information from the second implantable infusion pump device, and
      the second device comprises a second communication module configured to receive second infusion information from the first device; and
   a processor configured to:
      determine, based on the first infusion information and the second infusion information, that a total medicament infusion rate has fallen below an underdose threshold; and
      cause the first delivery mechanism or the second delivery mechanism to increase the total medicament infusion rate.

2. The system of claim 1, wherein the each of the first delivery mechanism and the second delivery mechanism comprises:
   a pressurized medicament reservoir comprising the medicament; and
   a medicament delivery valve, wherein opening the medicament delivery valve releases the medicament into tissue surrounding the respective delivery mechanism.

3. The system of claim 1, wherein the first delivery mechanism and the second delivery mechanism each comprises a refillable medicament reservoir.

4. The system of claim 1, wherein the medicament comprises baclofen or Treprostinil.

5. The system of claim 1, wherein each of the first delivery mechanism and the second delivery mechanism is configured to deliver the medicament through a shared catheter.

6. The system of claim 1, wherein the medicament comprises naloxone or epinephrine.

7. The implantable emergency management drug delivery system of claim 1, wherein the medicament comprises an opioid or treprostinil.

8. The system of claim 1, further comprising a physiological sensor, wherein the physiological sensor comprises an externally wearable device.

9. The system of claim 1, wherein the medicament comprises baclofen, and wherein the first delivery mechanism and the second delivery mechanism are configured to infuse the baclofen intrathecally.

10. The system of claim 1, wherein the first delivery mechanism and the second delivery mechanism each comprises a medicament pump and a refillable reservoir.

11. The system of claim 1, wherein the processor is further configured to output an alert.

12. The system of claim 11, wherein the alert comprises an indication of a physical location of the patient.

13. The system of claim 11, wherein the alert comprises an indication of the total medicament infusion rate.

14. The system of claim 1, wherein the first device comprises an implantable infusion pump, and wherein a malfunction of the implantable infusion pump causes the total medicament infusion rate to fall below the underdose threshold.

15. The system of claim 14, wherein the second device causes the first device to run diagnostics or reset to address the malfunction.

* * * * *